(12) United States Patent
Han et al.

(10) Patent No.: US 10,005,882 B2
(45) Date of Patent: Jun. 26, 2018

(54) METHOD FOR PREPARING MODIFIED BIODEGRADABLE POLYLMER, MODIFIED BIODEGRADABLE POLYMER PREPARED THEREFROM, AND BIODEGRADABLE STENT USING THE SAME

(71) Applicant: KOREA INSTITUTE OF SCIENCE AND TECHNOLOGY, Seoul (KR)

(72) Inventors: Dongkeun Han, Seoul (KR); Yoonki Joung, Seoul (KR); Jonghee Kang, Seoul (KR); Eunyoung Kang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 1 day.

(21) Appl. No.: 15/017,570

(22) Filed: Feb. 5, 2016

(65) Prior Publication Data
US 2017/0073464 A1 Mar. 16, 2017

(30) Foreign Application Priority Data
Sep. 10, 2015 (KR) .......................... 10-2015-0128584

(51) Int. Cl.
| | | |
|---|---|---|
| *A61K 6/083* | (2006.01) | |
| *A61K 6/00* | (2006.01) | |
| *C08G 63/91* | (2006.01) | |
| *A61L 31/14* | (2006.01) | |
| *C08K 5/1535* | (2006.01) | |
| *A61L 31/04* | (2006.01) | |

(52) U.S. Cl.
CPC .......... *C08G 63/912* (2013.01); *A61L 31/048* (2013.01); *A61L 31/148* (2013.01); *C08K 5/1535* (2013.01); *C08G 2230/00* (2013.01); *C08L 2201/06* (2013.01); *C08L 2203/02* (2013.01)

(58) Field of Classification Search
None
See application file for complete search history.

(56) References Cited

U.S. PATENT DOCUMENTS

2014/0288628 A1* 9/2014 Wang ...................... A61L 31/06
623/1.11

FOREIGN PATENT DOCUMENTS

| CN | 101851424 A | * 10/2010 | |
|---|---|---|---|
| JP | 2013-545509 A | 12/2013 | |
| KR | 10-2013-0104509 A | 9/2013 | |
| WO | WO 9620698 A2 | * 7/1996 | ........... A61K 9/5153 |
| WO | 2012/0511950 A1 | 4/2012 | |

OTHER PUBLICATIONS

Hydrolytic degradation of poly(D,L-lactide) as a function of en group: Carboxylic acid vs. Hyroxyl, Wiggins et al., Polymer, 47, 2006, 1960-1969.*
Lee et al. Synthesis and Degradation of End-Group-Functionalized Polylactide, Journal of Polymer Science,Dec. 25, 2000, Part A, vol. 39, pp. 973-982.
Communications of Korean Application No. 10-2015-0128584 dated Jul. 28, 2016, which corresponds to this application.
Pierre Erwan Le Marec et al., Influence of melt processing conditions on poly(lactic acid) degradation: Molar mass distribution and crystallization, Polymer Degradation and Stability, Oct. 16, 2014, pp. 353-363, vol. 110, Elsevier.
Jeffrey S. Wiggins et al., Hydrolytic degradation of poly(D,L-lactide) as a function of end group: Carboxylic acid vs. hydroxyl, Polymer, Feb. 3, 2006, pp. 1960-1969, Polymer vol. 47, Elsevier.
Soo-Hong Lee et al., Synthesis and Degradation of End-Group-Functionalized Polylactide, Journal of Polymer Science: Part A: Polymer Chemistry, 2001, pp. 973-985 , vol. 39, Korea.

* cited by examiner

*Primary Examiner* — Peter A Salamon
(74) *Attorney, Agent, or Firm* — Goldilocks Zone IP Law

(57) ABSTRACT

Disclosed are a method for preparing a modified biodegradable polymer by using various additives and plasticizers in a biodegradable polymer which is non-toxic to human bodies, a biodegradable polymer prepared therefrom, and a biodegradable stent prepared by using the biodegradable polymer. Specifically, it is possible to reduce a decrease in molecular weight resulting from a thermal degradation occurring during the solid-phase molding processing of a biodegradable polymer by coating a solution in which various additives are dissolved during the modification of the biodegradable polymer to convert the hydroxyl end group into a functional group of a carboxylic group or a different kind of hydroxyl group.

16 Claims, No Drawings

METHOD FOR PREPARING MODIFIED BIODEGRADABLE POLYLMER, MODIFIED BIODEGRADABLE POLYMER PREPARED THEREFROM, AND BIODEGRADABLE STENT USING THE SAME

CROSS-REFERENCE TO RELATED APPLICATION

Pursuant to 35 U.S.C. § 119(a), this application claims the benefit of earlier filing date and right of priority to Korean Application No. 10-2015-0128584, filed Sep. 10, 2015, the contents of which is incorporated by reference herein in its entirety.

TECHNICAL FIELD

The present invention relates to a method for preparing a modified biodegradable polymer by an additive, a modified biodegradable polymer prepared therefrom, and a biodegradable stent prepared by using the same.

BACKGROUND ART

A stent refers to a mesh tube implanted when the inner diameter of the artery or the blood vascular system becomes so narrow due to deposition of thrombus or lipids in the coronary arteries and the peripheral blood vessels that the flow of the bloodstream is not smooth, or when tumors occur in the non-vascular system such as the gastrointestinal tract, the esophagus, and the respiratory tract, or against stenosis occurring after a surgery. Conventionally, stents were manufactured by using metal or silicone materials, but these stents remain permanently in the human body, and thus need to be subjected to removal surgery because the remaining stents cause inflammation or other diseases.

In order to solve these problems, natural polymers or synthetic polymers and the like having biodegradability have been used. Biodegradable natural polymer materials have not only limited physical properties, but also problems in processability and mass-producibility, and thus have limitations in use. Meanwhile, synthetic polymers are generally used due to non-toxicity to human body, excellent mechanical properties and adjustable biodegradability. Accordingly, there have been extensive researches on biodegradable synthetic polymer materials. In particular, aliphatic polyesters having excellent physico-mechanical and hydrolytic characteristics have been the focus of various researches.

However, since biodegradable polymers have a much lower mechanical strength than metals and ceramics, the use thereof is limited. The low strength of biodegradable polymers is also due to a nature of polymer material, but is incurred by preparation methods thereof. That is, when a melt processing method such as extrusion, injection and compression moldings is used during the molding of a polymer, the breakdown of molecular chains is formed in a significant amount, and thus the molecular weight of the polymer is decreased, thereby reducing the final mechanical strength (Pierre Erwan Le Marec et al., Polym. Deg. Stab., 110, 353 (2014)).

Accordingly, various methods have been proposed in order to increase the mechanical strength of a biodegradable polymer.

For example, Korean Patent Publication No. 2001-0100249 A discloses a preparation method comprising a two-step process of vacuum compression molding and solid extrusion to reduce a decrease in molecular weight resulting from thermal degradation of biodegradable polymers. This method also describes process parameters adjustment to satisfy strength requirements of the polymer. The process parameters include a crystallinity of a vacuum compression molded product, a drawing ratio or a drawing speed and the like.

Meanwhile, Jeffrey S. Wiggins et al. suggested a method for modifying degradation of biodegradable polyesters, in which hydroxyl end group of the polymer is substituted with carboxylic acid. In this study, Wiggins et al showed that carboxylic acid end group functionality has an effect on degradation rate of the polymer and may reduce the weight loss compared to their hydroxyl-terminated analog (Jeffrey S. Wiggins et al., Polymer, 47, 1960 (2006)). However, since the hydroxyl end group is substituted by adding an acid anhydride as one of the polymerization components, the Wiggins' method has a problem in that the polymerization process becomes complicated.

Further, Lee et al. described the effect of different end group functionality of biodegradable polymer on degradation properties such as molecular weight reduction (Soo-Hong Lee et al., Journal of Polym. Sci. Part A: 39, 7 (2001)). For this purpose, Lee et al. prepared biodegradable polymers with various functional groups via pre-treatment process using substitution catalyst and analyzed thermal stability and thermal degradation rate etc. However, since a functional group is substituted by using a catalyst during the solution polymerization, this method has a problem in that the polymerization process becomes complicated.

DISCLOSURE OF THE INVENTION

According to these conventional technologies, the molecular weight is controlled through a processing method without the modification of a biodegradable polymer material or a biodegradable polymer is prepared by modifying the biodegradable polymer material through the solution polymerization before the processing, and then processing the biodegradable polymer material, therefore the process becomes complicated. Also, the use of a catalyst may enhance the substitution effects, but there is limitation in the use thereof because some catalysts have toxic potential to human body.

Therefore, an object of the present invention is to provide a method for preparing a modified biodegradable polymer, which solves the problems described above, and may reduce a decrease in molecular weight resulting from the thermal degradation during the solid-phase mixing and extrusion molding processing and control the hydrolytic biodegradability, and may significantly improve mechanical properties.

To achieve these and other advantages and in accordance with the purpose of the present invention, as embodied and broadly described herein, there is provided a method for preparing a modified biodegradable polymer according to the present invention includes:

providing a biodegradable polymer including a hydroxyl end group;

pre-coating the biodegradable polymer with a solution prepared by dissolving an additive for substituting a hydroxyl end group of the biodegradable polymer with a carboxylic group or another hydroxyl group in a solvent; and substituting the hydroxyl end group of the biodegradable polymer with a carboxylic group or another hydroxyl group by subjecting the coated biodegradable polymer to solid-phase mixing extrusion molding.

In the method for preparing a biodegradable polymer according to the present invention, the biodegradable polymer including a hydroxyl end group is selected from the group consisting of poly(glycolic acid) (PGA), poly(L-lactic acid) (PLLA), poly(D-lactic acid) (PDLA), poly(D,L-lactic acid) (PDLLA), poly(ε-caprolactone) (PCL), poly(lactic acid-co-glycolic acid) (PLGA), poly(L-lactic acid-co-ε-caprolactone) (PLCL), tyrosine polycarbonate, salicylic acid-containing polymer, polyanhydride, polyorthoester, polydioxanone, cellulose acetate butyrate, triacetin and cellulose triacetate.

In the method of the present invention, the biodegradable polymer has a molecular weight in a range of 5,000 to 1,000,000, preferably 10,000 to 500,000.

In the method of the present invention, the additive is used in an amount of 0.5 to 30 wt %, preferably 1 to 10 wt % based on the biodegradable polymer.

In the method of the present invention, the additive used to convert the hydroxyl end group of the biodegradable polymer into a carboxylic group is an aliphatic acid anhydride, an alicyclic acid anhydride, an aromatic acid anhydride, or a halogen-based acid anhydride, and is specifically selected from the group consisting of maleic anhydride, citraconic anhydride, 2,3-dimethylmaleic anhydride, cis-aconitic anhydride, phenylmaleic anhydride, succinic anhydride, dodecyl succinic anhydride, methylsuccinic anhydride, butylsuccinic anhydride, 2-octen-1-ylsuccinic anhydride, phenylsuccinic anhydride, 2-benzylsuccinic anhydride, triacetin and mixtures thereof.

In the method of the present invention, the additive used to convert the hydroxyl group at the end of the biodegradable polymer into another hydroxyl group is glycidyl ether, and is specifically selected from the group consisting of diglycidyl ether, diethylene glycol diglycidyl ether, resorcinol diglycidyl ether, bisphenol A diglycidyl ether, bisphenol A propoxylate diglycidyl ether, bisphenol F diglycidyl ether, poly(ethylene glycol) diglycidyl ether, poly(propylene glycol) diglycidyl ether, 1,2-propanediol diglycidyl ether, 1,4-butanediol diglycidyl ether, neopentyl glycol diglycidyl ether, 1,4-cyclohexanedimethanol diglycidyl ether (mixture of cis and trans), and mixtures thereof.

In the method of the present invention, during the solution coating of the biodegradable polymer, it is possible to further add a plasticizer selected from the group consisting of isosorbide aliphatic acid ester, triethyl citrate, tributyl citrate, polyethylene glycol (PEG), Pluronic F series, di(2-ethylhexyl)phtalate (DEHP), maleic anhydride grafted polyethylene (PE-g-MAH), maleic anhydride grafted polypropylene (PP-g-MAH), maleic anhydride grafted ethylene butyl acrylate (EBA-g-MAH) or copolymers thereof thereto. The plasticizer may be used in an amount of 0.5 to 30 wt %, preferably 1 to 10 wt % based on the biodegradable polymer.

In the method of the present invention, a solution coating method is used in order to coat an additive on the surface of a biodegradable polymer. A solvent capable of dissolving the additive is selected from the group consisting of acetone, methanol, ethanol, hexane, acetonitrile, ethyl acetate, tetrahydrofuran, dioxane, diethyl ether, methyl tert-butyl ether, methyl ethyl ketone, toluene, or combinations thereof.

The additive has a concentration of 1 to 50 wt % based on the solvent, and the biodegradable polymer is coated with the additive solution at a temperature of room temperature to 100° C.

In the method according to the present invention, the temperature during the molding processing of the biodegradable polymer is 150 to 250° C., preferably 180 to 220° C.

The present invention also relates to a modified biodegradable polymer and a biodegradable stent using the same. The modified biodegradable polymer can be prepared by the method described above.

By the method for preparing a biodegradable polymer according to the present invention, it is possible to inhibit formation of rings and breakdown of chains in the polymer resulting from back-biting reactions due to a carboxylic group or a hydroxyl group by using a solution coating method to uniformly apply an additive on the surface of the biodegradable polymer and using the additive to substitute a hydroxyl end group of the biodegradable polymer with a carboxylic group or another hydroxyl group. Further, it is possible to inhibit a decrease in molecular weight resulting from the thermal degradation of the biodegradable polymer by means of a simple method without employing an additional process. Furthermore, in the method of the present invention, a polymer having excellent mechanical strength may be prepared by polymerizing a biodegradable polymer through an esterification reaction between a carboxylic group and a hydroxyl end group of the polymer.

The mechanical strength of the biodegradable polymer may be improved thereby, and it is also possible to provide a biodegradable polymer capable of adjusting mechanical properties and biodegradability depending on the substitution ratio of a hydroxyl end group of the biodegradable polymer.

Further, the biodegradable polymer according to the present invention may be suitably used as a biomaterial which requires high strength, particularly, a material for a stent because mechanical properties including tensile strength and elongation may be improved by modifying the biodegradable polymer by means of only a simple process without a separate processing process or a pre-treatment before the processing. A stent prepared from the biodegradable polymer according to the present invention has not only a sufficient mechanical strength, but also an effect that the degradation period of the stent may be controlled by adjusting the biodegradability of the biodegradable polymer.

MODES FOR CARRYING OUT THE PREFERRED EMBODIMENTS

A method for preparing a biodegradable polymer according to the present invention includes: providing a biodegradable polymer including a hydroxyl end group;

pre-coating the biodegradable polymer with a solution prepared by dissolving an additive in a solvent in order to substitute a hydroxyl end group of the biodegradable polymer with a carboxylic group or another hydroxyl group; and substituting the hydroxyl end group of the biodegradable polymer with a carboxylic group or another hydroxyl group by subjecting the coated biodegradable polymer to solid-phase mixing extrusion molding.

In the method, it is preferred that the biodegradable polymer including a hydroxyl end group has a molecular weight in a range of 5,000 to 1,000,000. This is because sufficient mechanical properties may not be obtained when the molecular weight is less than 5,000, and it is difficult to perform processing when the molecular weight is more than 1,000,000. As the biodegradable polymer, there is used a polymer selected from the group consisting of poly(glycolic acid) (PGA), poly(L-lactic acid) (PLLA), poly(D-lactic acid) (PDLA), poly(D,L-lactic acid) (PDLLA), poly(ε-caprolactone) (PCL), poly(lactic acid-co-glycolic acid) (PLGA), poly(L-lactic acid-co-ε-caprolactone (PLCL), tyrosine polycarbonate, salicylic acid-containing polymer, polyamino acid, polyanhydride, polyorthoester, polydioxanone, polyphosphazene, cellulose acetate butyrate, and cellulose triacetate.

In the method of the present invention, an additive used to convert a hydroxyl end group of the biodegradable polymer into a carboxylic group or another hydroxyl group, that is, a secondary or tertiary hydroxyl group includes an aliphatic acid anhydride, an alicyclic acid anhydride, an aromatic acid anhydride, a halogen-based acid anhydride, and glycidyl ethers.

Specifically, the additive used to convert the hydroxyl end group of the biodegradable polymer into a carboxylic group is an aliphatic acid anhydride, an alicyclic acid anhydride, an aromatic acid anhydride, or a halogen-based acid anhydride, and is preferably selected from the group consisting of maleic anhydride, citraconic anhydride, 2,3-dimethylmaleic anhydride, cis-aconitic anhydride, phenylmaleic anhydride, succinic anhydride, dodecyl succinic anhydride, methylsuccinic anhydride, butylsuccinic anhydride, 2-octen-1-ylsuccinic anhydride, phenylsuccinic anhydride, 2-benzylsuccinic anhydride, triacetin and mixtures thereof.

In addition, the additive used to convert the hydroxyl end group of the biodegradable polymer into another hydroxyl group is glycidyl ether, and is preferably selected from the group consisting of diglycidyl ether, diethylene glycol diglycidyl ether, resorcinol diglycidyl ether, bisphenol A diglycidyl ether, bisphenol A propoxylate diglycidyl ether, bisphenol F diglycidyl ether, poly(ethylene glycol) diglycidyl ether, poly(propylene glycol) diglycidyl ether, 1,2-propanediol diglycidyl ether, 1,4-butanediol diglycidyl ether, neopentyl glycol diglycidyl ether, 1,4-cyclohexanedimethanol diglycidyl ether (mixture of cis and trans), and mixtures thereof.

The additive is used in an amount of 0.5 to 30 wt %, preferably 1 to 10 wt % based on the biodegradable polymer. When an additive is added in an amount of less than 0.5 wt % based on the biodegradable polymer, the effects of adding the additive may not be exhibited, and when the additive is added in an amount of more than 30 wt %, an unreacted additive is present, and a decrease in molecular weight may occur due to the presence of the unreacted additive. In the method according to the present invention, it is possible not only to efficiently inhibit the thermal degradation of the polymer during the processing by using an additive to convert the hydroxyl end group of the biodegradable polymer with a carboxylic group or another hydroxyl group, but also to control the biodegradability of the biodegradable polymer by adjusting amount of the additive thereby modifying the carboxylic group or another hydroxyl group substituted at the end of the biodegradable polymer.

Furthermore, in the method of the present invention, a plasticizer may further be used in order to improve thermal stability of the biodegradable polymer and increase the dispersibility thereof in the polymer matrix after being dried by increasing the compatibility. The plasticizer is selected from the group consisting of isosorbide aliphatic acid ester, triethyl citrate, tributyl citrate, polyethylene glycol (PEG), Pluronic F series, di(2-ethylhexyl)phtalate (DEHP), maleic anhydride grafted polyethylene (PE-g-MAH), maleic anhydride grafted polypropylene (PP-g-MAH), maleic anhydride grafted ethylene butyl acrylate (EBA-g-MAH) or copolymers thereof.

When the plasticizer is used in an amount of less than 0.5 wt % based on the biodegradable polymer, the plasticizing effect may not be exhibited, and when the plasticizer is used in an amount of more than 30 wt % based on the biodegradable polymer, appropriate mechanical properties are not obtained. Therefore, the plasticizer is used in an amount of 0.5 to 30 wt %, preferably 1 to 10 wt % based on the biodegradable polymer.

When a plasticizer is used in the method for preparing a biodegradable polymer according to the present invention, the plasticizer is solution-coated on the polymer in company with the additive for converting a hydroxyl group of the biodegradable polymer.

In the method for preparing a biodegradable polymer according to the present invention, an additive for substituting a hydroxyl end group of biodegradable polymer with a carboxylic group or another hydroxyl group is coated on the biodegradable polymer by using a solution coating method. The solution coating method includes putting a biodegradable polymer in the form of a pellet in a solution prepared by dissolving an additive in a solvent, stirring the resulting mixture, and then removing the solvent by means of evaporation. Unlike solvent cast coating, there is no remaining solvent in solution coating. Since the additive does not precipitated during the drying process, it is possible to uniformly distribute the additive on the polymer surface.

The biodegradable polymer having the surface thereof coated with the additive as described above is modified by substituting a hydroxyl end group with another hydroxyl group or a carboxylic group through a solid-phase extrusion molding process after the polymer is dried.

Specifically, in the solid-phase extrusion molding, the mixing is carried out in a cylindrical tube, and the processing temperature exceeds melting point of the biodegradable polymer used. It is preferred that the mixing is carried out within 1 to 10 minutes. When the mixing time is less than 1 minute, the material is not sufficiently molten, and thus it is difficult to perform the processing, and when the time is more than 10 minutes, the thermal degradation is promoted, and thus the molecular weight is decreased. The mixed polymer is solid-phase extruded under an extrusion pressure of 10 to 100 MPA at a temperature of 150 to 250° C. At this time, when the extrusion temperature is less than 150° C., it is difficult to perform the processing due to high viscosity, and when the extrusion temperature is more than 250° C., a decrease in molecular weight resulting from the thermal degradation predominantly occurs. Therefore, it is preferred that the extrusion is carried out at 150 to 250° C. If extrusion pressure is less than 10 MPa, the extrusion time is prolonged, and thus the residence time in the device is increased, and when an extrusion pressure is more than 100 MPa, the extrusion time is shortened, but a polymer having high viscosity may impose overloading on the device.

Hereinafter, the contents of the present invention will be described in more detail through the Examples.

The Examples are only for describing the present invention, and it will be obvious to those skilled in the art that the scope of the present invention is not interpreted to be limited by these Examples.

Example 1

Maleic anhydride (0.03 g) was dissolved in 1 ml of acetone. A pellet of a poly(L-lactic acid) (PLLA) having a molecular weight of 300,000 (3.0 g) was put into the dissolved solution, the resulting mixture was stirred, and then the solvent was removed through an evaporator. Coating was performed while the resulting product was rotated at 150 rpm per minute for 30 minutes by using a rotary evaporator. The additive was coated on the surface of the polymer pellet by the solution coating method as described above, and then dried at room temperature for 12 hours. The polymer pellet coated with additive was dried at room temperature and then vacuum-dried at 60° C. for 24 hours. A test specimen was prepared by extruder to extrude a biodegradable polyester polymer pellet having a surface thereof on which the additive material is homogeneously distributed under a pressure of 70 MPa at a melt temperature of 200° C. by means of the solid-phase mixing extrusion molding.

The molecular weight of a biodegradable polymer degraded by heat and the processing conditions during the extrusion processing are shown in Table 1. As can be seen from Table 1, the molecular weight loss of biodegradable polymer was effectively prevented. In terms of elongation and tensile modulus, excellent results were confirmed. The tensile strength and the elongation were evaluated by using an ASTM D638 method. The molecular weight was measured by using a Waters 410 gel permeation chromatography (GPC) to dissolve the biodegradable polymer in a chloroform solvent, and a change in molecular weight before and after the extrusion is shown.

Example 2

A test specimen was prepared in the same manner as in the method of Example 1, except that a poly(D-lactic acid) (PDLA) having a molecular weight of 200,000 (3.0 g) as the biodegradable polymer and dimethylmaleic anhydride (0.09 g) as the additive were used while being dissolved in methanol. The molecular weight of a biodegradable polymer degraded by heat and the processing conditions during the extrusion processing are shown in Table 1. As can be seen from Table 1, excellent results were confirmed.

Example 3

A test specimen was prepared in the same manner as in the method of Example 1, except that a poly(D,L-lactic acid) (PDLLA) having a molecular weight of 400,000 (3.0 g) as the biodegradable polymer and phenylmaleic anhydride (0.06 g) as the additive were used while being dissolved in ethanol. The molecular weight of a biodegradable polymer degraded by heat and the processing conditions during the extrusion processing are shown in Table 1. As can be seen from Table 1, excellent results were confirmed.

Example 4

A test specimen was prepared in the same manner as in the method of Example 1, except that poly(ε-caprolactone) (PCL) having a molecular weight of 600,000 (3.0 g) as the biodegradable polymer and succinic anhydride (0.09 g) as the additive were used while being dissolved in acetonitrile. The molecular weight of a biodegradable polymer degraded by heat and the processing conditions during the extrusion processing are shown in Table 1. As can be seen from Table 1, excellent results were confirmed.

Example 5

A test specimen was prepared in the same manner as in the method of Example 1, except that a poly(lactic acid-co-glycolic acid) (PLGA) having a molecular weight of 320,000 (3.0 g) as the biodegradable polymer and butylsuccinic anhydride (0.03 g) as the additive were used while being dissolved in tetrahydrofuran. The molecular weight of a biodegradable polymer degraded by heat and the processing conditions during the extrusion processing are shown in Table 1. As can be seen from Table 1, excellent results were confirmed.

Example 6

A test specimen was prepared in the same manner as in the method of Example 1, except that poly(L-lactic acid-co-ε-caprolactone) (PLCL) having a molecular weight of 220,000 (3.0 g) as the biodegradable polymer and propylene diglycidyl ether (0.09 g) as the additive were used while being dissolved in hexane. The molecular weight of a biodegradable polymer degraded by heat and the processing conditions during the extrusion processing are shown in Table 1. As can be seen from Table 1, excellent results were confirmed.

Example 7

A test specimen was prepared in the same manner as in the method of Example 1, except that a polyanhydride having a molecular weight of 430,000 (3.0 g) as the biodegradable polymer and bisphenol A propoxylate diglycidyl ether (0.06 g) as the additive were used while being dissolved in diethyl ether. The molecular weight of a biodegradable polymer degraded by heat and the processing conditions during the extrusion processing are shown in Table 1. As can be seen from Table 1, excellent results were confirmed.

Example 8

A test specimen was prepared in the same manner as in the method of Example 1, except that a polyorthoester having a molecular weight of 100,000 (3.0 g) was used, maleic anhydride (0.09 g) as the additive was used while being dissolved in dioxane, and an isosorbide aliphatic acid ester compound (0.03 g) as a plasticizer other than the additive was added. The molecular weight of a biodegradable polymer degraded by heat and the processing conditions during the extrusion processing are shown in Table 1. As can be seen from Table 1, excellent results were confirmed.

Example 9

A test specimen was prepared in the same manner as in the method of Example 1, except that a polydioxanone having a molecular weight of 330,000 (3.0 g) as the biodegradable polymer and succinic anhydride (0.09 g) as the additive were used while being dissolved in ethyl acetate, and Pluronic F 127 (0.03 g) as a plasticizer was added. The molecular weight of a biodegradable polymer degraded by heat and the processing conditions during the extrusion processing are shown in Table 1. As can be seen from Table 1, excellent results were confirmed.

Example 10

A test specimen was prepared in the same manner as in the method of Example 1, except that a poly(L-lactic acid) (PLLA) having a molecular weight of 200,000 (3.0 g) as the polymer and resorcinol diglycidyl ether (0.09 g) as the additive were used while being dissolved in toluene, and tributyl citrate (0.03 g) as a plasticizer was added. The molecular weight of a biodegradable polymer degraded by heat and the processing conditions during the extrusion processing are shown in Table 1. As can be seen from Table 1, excellent results were confirmed.

Example 11

A test specimen was prepared in the same manner as in the method of Example 1, except that a poly(D,L-lactic acid) (PDLLA) having a molecular weight of 300,000 (3.0 g) as the polymer and bisphenol A propoxylate diglycidyl ether (0.09 g) as the additive were used while being dissolved in methyl ethyl ketone, and polyethylene glycol (0.03 g) as a plasticizer was added. The molecular weight of a biodegradable polymer degraded by heat and the processing conditions during the extrusion processing are shown in Table 1. As can be seen from Table 1, excellent results were confirmed.

Example 12

A test specimen was prepared in the same manner as in the method of Example 1, except that a poly(ε-caprolactone) (PCL) having a molecular weight of 600,000 (3.0 g) as the biodegradable polymer and triacetin (0.09 g) as the additive were used. The molecular weight of a biodegradable polymer degraded by heat and the processing conditions during the extrusion processing are shown in Table 1. As can be seen from Table 1, excellent results in terms of prevention of a decrease in molecular weight, tensile strength, and elongation were confirmed.

Comparative Example 1

A test specimen was prepared by extruding a pellet of a poly(L-lactic acid) (PLLA) having a molecular weight of 300,000 (3.0 g) without any additive under a pressure of 70 MPa at a melt temperature 200° C. by means of a solid-phase mixing extrusion molding. The molecular weight of a biodegradable polymer degraded by heat and the processing conditions during the extrusion processing are shown in Table 1. As can be seen from Table 1, poor results in terms of prevention of a decrease in molecular weight, tensile strength, and elongation were confirmed.

Comparative Example 2

A test specimen was prepared in the same manner as in the method of Example 1, except that a pellet of a poly-L-lactic acid having a molecular weight of 300,000 (3.0 g) and the existing di(2-ethylhexyl)phthalate (DEHP) (0.03 g) as a plasticizer instead of the additive were used. The molecular weight of a biodegradable polymer degraded by heat and the processing conditions during the extrusion processing are shown in Table 1. As can be seen from Table 1, poor results in terms of prevention of a decrease in molecular weight, tensile strength, and elongation were confirmed.

TABLE 1

Change in molecular weight and mechanical properties after extrusion molding processing

| | Loss of molecular weight (%) | Tensile strength (MPa) | Elongation (%) |
|---|---|---|---|
| Example 1 | 10 | 67 | 150 |
| Example 2 | 13 | 65 | 145 |
| Example 3 | 15 | 62 | 180 |
| Example 4 | 19 | 58 | 190 |
| Example 5 | 16 | 59 | 160 |
| Example 6 | 15 | 59 | 200 |
| Example 7 | 19 | 58 | 170 |
| Example 8 | 17 | 58 | 180 |
| Example 9 | 16 | 58 | 170 |
| Example 10 | 17 | 60 | 180 |
| Example 11 | 15 | 58 | 190 |
| Example 12 | 11 | 60 | 140 |
| Comparative Example 1 | 44 | 40 | 100 |
| Comparative Example 2 | 36 | 42 | 110 |

What is claimed is:

1. A method for preparing a modified biodegradable polymer, the method comprising:
   providing a biodegradable polymer comprising a hydroxyl end group;
   pre-coating the biodegradable polymer with a solution prepared by dissolving an additive in a solvent in order to substitute a hydroxyl end group of the biodegradable polymer with a carboxylic group or another hydroxyl group, wherein the pre-coating is performed by using a rotary evaporator; and
   substituting the hydroxyl end group of the biodegradable polymer with a carboxylic group or another hydroxyl group by subjecting the coated biodegradable polymer to solid-phase mixing extrusion molding.

2. The method of claim 1, wherein the biodegradable polymer having a hydroxyl end group is selected from the group consisting of poly(glycolic acid) (PGA), poly(L-lactic acid) (PLLA), poly(D-lactic acid) (PDLA), poly(D,L-lactic acid) (PDLLA), poly(ε-caprolactone) (PCL), poly(lactic acid-co-glycolic acid) (PLGA), poly(L-lactic acid-co-ε-caprolactone) (PLCL), tyrosine polycarbonate, salicylic acid-containing polymer, polyamino acid, polyanhydride, polyorthoester, polydioxanone, polyphosphazene, cellulose acetate butyrate, and cellulose triacetate.

3. The method of claim 1, wherein the biodegradable polymer has a molecular weight of 5,000 to 1,000,000.

4. The method of claim 1, wherein an additive used to convert the hydroxyl end group of the biodegradable polymer into a carboxylic group is an aliphatic acid anhydride, an alicyclic acid anhydride, an aromatic acid anhydride, or a halogen-based acid anhydride.

5. The method of claim 4, wherein the additive is selected from the group consisting of maleic anhydride, citraconic anhydride, 2,3-dimethylmaleic anhydride, cis-aconitic anhydride, phenylmaleic anhydride, succinic anhydride, dodecyl succinic anhydride, methylsuccinic anhydride, butylsuccinic anhydride, 2-octen-1-ylsuccinic anhydride, phenylsuccinic anhydride, 2-benzylsuccinic anhydride, triacetin, and mixtures thereof.

6. The method of claim 1, wherein an additive used to convert the hydroxyl end group of the biodegradable polymer into another hydroxyl group is glycidyl ether.

7. The method of claim 6, wherein the additive is selected from the group consisting of diglycidyl ether, diethylene glycol diglycidyl ether, resorcinol diglycidyl ether, bisphenol A diglycidyl ether, bisphenol A propoxylate diglycidyl ether, bisphenol F diglycidyl ether, poly(ethylene glycol) diglycidyl ether, poly(propylene glycol) diglycidyl ether, 1,2-propanediol diglycidyl ether, 1,4-butanediol diglycidyl ether, neopentyl glycol diglycidyl ether, 1,4-cyclohexanedimethanol diglycidyl ether (mixture of cis and trans), and mixtures thereof.

8. The method of claim 7, wherein the additive is used in an amount of 0.5 to 30 wt % based on the biodegradable polymer.

9. The method of claim 1, wherein during the solution coating of the biodegradable polymer, a plasticizer is added and the plasticized is selected from the group consisting of isosorbide aliphatic acid ester, triethyl citrate, tributyl citrate, polyethylene glycol (PEG), Pluronic F series, di(2-ethylhexyl)phthalate (DEHP), maleic anhydride grafted polyethylene (PE-g-MAH), maleic anhydride grafted polypropylene (PP-g-MAH), maleic anhydride grafted ethylene butyl acrylate (EBA-g-MAH) or copolymers thereof thereto.

10. The method of claim 9, wherein the plasticizer is used in an amount of 0.5 to 30 wt % based on the biodegradable polymer.

11. The method of claim 1, wherein a solvent capable of the dissolving the additive is selected from the group consisting of acetone, methanol, ethanol, hexane, acetonitrile, ethyl acetate, tetrahydrofuran, dioxane, diethyl ether, methyl tert-butyl ether, methyl ethyl ketone, toluene, or combinations thereof.

12. The method of claim 11, wherein a concentration of the additive is 1 to 50 wt % based on the solvent.

13. The method of claim 11, wherein the biodegradable polymer is coated with the additive solution at a temperature of room temperature to 100° C.

14. The method of claim 1, wherein a temperature during the molding processing is 150 to 250° C.

15. A modified biodegradable polymer prepared by the method of claim 1.

16. A stent prepared by using the biodegradable polymer of claim 15.

* * * * *